US011599343B2

(12) United States Patent
Dominick et al.

(10) Patent No.: US 11,599,343 B2
(45) Date of Patent: Mar. 7, 2023

(54) METHODS AND DEVICES FOR MODIFYING A RUNTIME ENVIRONMENT OF IMAGING APPLICATIONS ON A MEDICAL DEVICE

(71) Applicant: Siemens Healthcare GmbH, Erlangen (DE)

(72) Inventors: Lutz Dominick, Eggolsheim (DE); Vladyslav Ukis, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 975 days.

(21) Appl. No.: 16/403,809

(22) Filed: May 6, 2019

(65) Prior Publication Data
US 2019/0347186 A1    Nov. 14, 2019

(30) Foreign Application Priority Data
May 8, 2018   (EP) .................................. 18171239

(51) Int. Cl.
*G06F 8/41*       (2018.01)
*G16H 40/40*      (2018.01)
(Continued)

(52) U.S. Cl.
CPC .............. *G06F 8/443* (2013.01); *G06F 8/64* (2013.01); *G06F 8/71* (2013.01); *G06F 11/302* (2013.01);
(Continued)

(58) Field of Classification Search
None
See application file for complete search history.

(56) References Cited

U.S. PATENT DOCUMENTS

2009/0007073 A1    1/2009  Huang et al.
2012/0079497 A1*   3/2012  Gangemi .............. G06F 9/5011
                                                    718/104
(Continued)

OTHER PUBLICATIONS

Lan, "A Model-Based Autonomous Engine for Application Runtime Environment Configuration and Deployment in PaaS Cloud", 2014, IEEE 6th International Conference on Cloud Computing Technology and Science (Year: 2014).*
(Continued)

*Primary Examiner* — Hossain M Morshed

(74) *Attorney, Agent, or Firm* — Harness, Dickey & Pierce, P.L.C.

(57) ABSTRACT

A method, an improvement node, a system and a computer program for computing an improvement result for a runtime environment of at least one application, on a device in a medical context. An embodiment of the method includes detecting a state of the runtime environment on the device; accessing a database with the state detected, to retrieve a corresponding at least one candidate improvement result; using the at least one candidate improvement result retrieved, for test-wise execution on a test infrastructure in which the state of the runtime environment detected is provided identically; measuring improvement parameters of the test-wise execution; and adding, upon the improvement parameters measured meeting defined requirements, candidate improvement results, of the at least one corresponding
(Continued)

candidate improvement result retrieved, for which the improvement parameters measured meet defined requirements.

26 Claims, 3 Drawing Sheets

(51) Int. Cl.
    *G06F 16/2455*     (2019.01)
    *G06F 11/30*     (2006.01)
    *G06F 11/34*     (2006.01)
    *G06F 11/36*     (2006.01)
    *G06F 8/61*     (2018.01)
    *G06F 8/71*     (2018.01)

(52) U.S. Cl.
    CPC ...... *G06F 11/3013* (2013.01); *G06F 11/3495* (2013.01); *G06F 11/3664* (2013.01); *G06F 11/3672* (2013.01); *G06F 11/3688* (2013.01); *G06F 11/3692* (2013.01); *G06F 16/2455* (2019.01); *G16H 40/40* (2018.01)

(56) References Cited

U.S. PATENT DOCUMENTS

| | | | |
|---|---|---|---|
| 2012/0151187 A1* | 6/2012 | De Smet | G06F 8/52 |
| | | | 712/E9.016 |
| 2012/0317558 A1* | 12/2012 | Agarwal | G06F 8/443 |
| | | | 717/149 |
| 2016/0321046 A1* | 11/2016 | Pizlo | G06F 8/443 |
| 2017/0286253 A1* | 10/2017 | Che | G06F 11/3636 |
| 2018/0329956 A1* | 11/2018 | Mittal | G06F 16/24549 |
| 2018/0349159 A1* | 12/2018 | Boutnaru | G06F 9/5027 |
| 2019/0347186 A1* | 11/2019 | Dominick | G06F 8/443 |

OTHER PUBLICATIONS

Lan, "A Model-Based Autonomous Engine for Application Runtime Environment Configuration and Deployment in PaaS Cloud", 2014, IEEE (Year: 2014).*
European Office Action dated Oct. 29, 2020.
European Search Report for European Application No. 18171239 dated Oct. 23, 2018.

* cited by examiner

METHODS AND DEVICES FOR MODIFYING A RUNTIME ENVIRONMENT OF IMAGING APPLICATIONS ON A MEDICAL DEVICE

PRIORITY STATEMENT

The present application hereby claims priority under 35 U.S.C. § 119 to European patent application number EP 18171239.9 filed May 8, 2018, the entire contents of which are hereby incorporated herein by reference.

FIELD

Embodiments of the present invention generally refer to an improvement of a runtime environment for a medical application on a medical device, in particular an imaging device.

BACKGROUND

Modern medical application environments are complex and use a variety of different devices, from different manufacturers, in a heterogeneous landscape and infrastructure with heterogeneous functions and applications and often in a non-standardized manner. This leads to challenges when technical improvements need to be implemented with respect to the information technological infrastructure. Each system has to be considered separately and improvements with respect to the runtime environment are to be implemented dedicatedly for each device or system.

SUMMARY

The inventors have discovered that there is a need in the art to overcome the problems of state of the art systems. In particular, an automatic computation of infrastructural improvements should be provided taking into account the specific device with installed applications and with its runtime environment, wherein the improvements should be pre-tested in the very runtime environment of the device in order to be able to concretely measure the impact of the improvement on the device itself.

Advantageous embodiments are the subject matter of the dependent claims, the description and the figures.

A first embodiment of the present application refers to a method for computing an improvement result for a runtime environment of at least one application, on an imaging or another device in a medical context, comprising:
  detecting a state of the runtime environment on the device;
  accessing a database with the state detected, to retrieve a corresponding at least one candidate improvement result;
  using the at least one candidate improvement result retrieved, for test-wise execution on a test infrastructure in which the state of the runtime environment detected is provided identically;
  measuring improvement parameters of the test-wise execution; and
  adding, upon the improvement parameters measured meeting defined requirements, candidate improvement results, of the at least one corresponding candidate improvement result retrieved, for which the improvement parameters measured meet defined requirements.

The method of at least one embodiment is computer implemented. The computer implemented method may be stored on a computer readable medium or memory. All steps are executed on a computing device or a network thereof. Thus, the method is executed by employing at least one processing entity configured to execute computer-executable instructions stored in a memory to perform the steps, mentioned above.

Another embodiment of the invention therefore also refers to a computer program with program code for executing an embodiment of the method mentioned above, upon the computer program being executed on an electronic device. The computer program may be provided via download from a server. Further, the computer program may be executed on a sever for a client by assessing a link or a http interface on a web-browser on the client.

The computer program may be offered, placed on market, used, imported and/or stored as (and thus may be part of) a computer program product. Thus, the computer program may be provided on a non-transitory storage medium (computer readable medium, like a computer disc or a memory stick etc.). Alternatively, the computer program may be provided via download via a respective network connection to a server, which stores the computer program by providing a link to the server with the computer program stored thereon. A "computer-readable medium" or "storage medium" can be any device that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium can include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CDROM).

Another embodiment of the application is directed to a cloud-based improvement node for computing an improvement result for a runtime environment of at least one application, on a device in a medical context, comprising:
  a state interface, adapted to detect a state of the runtime environment on the device;
  a database interface, for a database in which a correlation is stored between states, improvement targets and corresponding candidate improvement result, to permit access to the database with the detected state in order to retrieve
  at least one corresponding candidate improvement result;
  a test infrastructure, provided for each of a plurality of different devices, dedicatedly, by representing the detected state of the runtime environment of a respective device, the test infrastructure being usable for test-wise execution of the at least one candidate improvement result retrieved;
  a measurement unit, adapted to measure improvement parameters during the test-wise execution on the test infrastructure; and
  an output interface, adapted for providing the improvement result, wherein the improvement result includes candidate improvement results for which the improvement parameters measured meet defined requirements.

Another embodiment of the application is directed to a system for computing an improvement result for a device within a network of devices to be used in a medical context, the system comprising:

an improvement node according to an embodiment of the application;

a plurality of devices, each having its runtime environment for execution of a plurality of applications; and a database.

The following detailed description of the figures uses the drawings to discuss illustrative embodiments, which are not to be construed as restrictive, along with the features and further advantages thereof.

DETAILED DESCRIPTION OF THE EXAMPLE EMBODIMENTS

Figure 1:
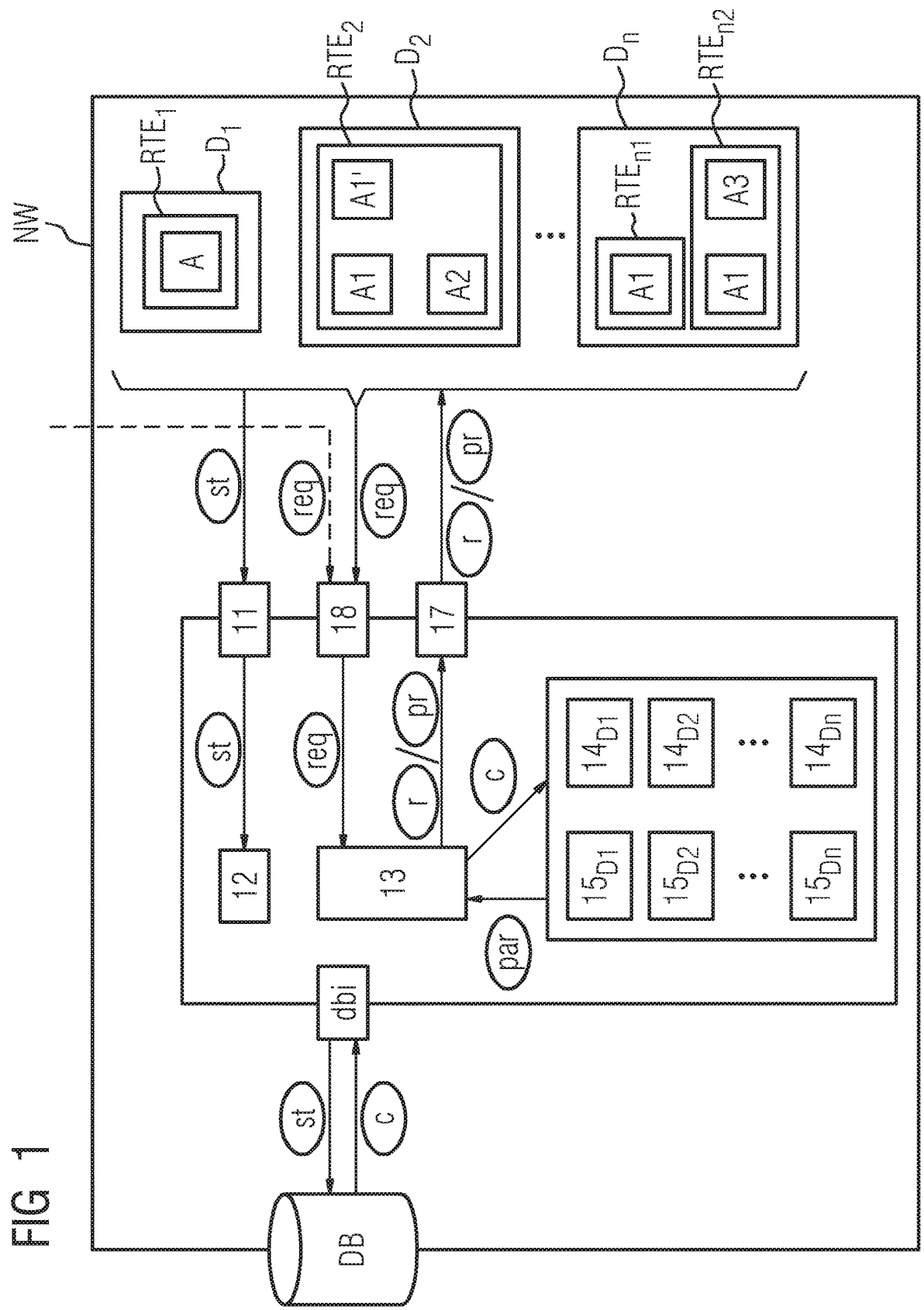
FIG. 1 shows an overview figure for an improvement node and respective message exchange for improvement computations for different devices.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

A first embodiment of the present application refers to a method for computing an improvement result for a runtime environment of at least one application, on an imaging or another device in a medical context, comprising:

detecting a state of the runtime environment on the device;

accessing a database with the detected state—or with improvement targets, which may be deduced from the state and/or which are related to the detected state—in order to retrieve at least one corresponding candidate improvement result;

using the retrieved candidate improvement result for test-wise execution on a test infrastructure in which the detected state of the runtime environment is provided identically;

measuring improvement parameters of (and during) the test-wise execution and if the measured improvement parameters meet predefined requirements; and adding the candidate improvement result to the (final) improvement result for providing the same as final improvement result.

An idea behind an embodiment of the invention is to utilize existing data of reference applications and/or reference runtime environments for computing an improvement result as suggestion (or improvement candidate) and to automatically test this improvement suggestion in a test infrastructure which exactly mirrors the runtime environment of the very application which should be improved. During the test, improvement parameters are measured for the application and the device. In case the measured improvement parameters of the test are within a pre-defined range, then the improvement candidate will be processed as improvement result and will be provided to the device for implementation.

An important advantage of a proposed solution of an embodiment is that only those improvements will be selected as improvement result which mean a realistic advancement in the respective context or runtime environment. For example, if the improvement result includes adding processor capacity, this will only be expedient and appropriate for e.g. a thin device, where processor capacity was tested to be not sufficient, whereas the improvement result will not be expedient and appropriate for a server device which was tested and measured to have sufficient processing resources. This is possible, because the improvement candidates are tested first on a dedicated infrastructure in order to measure improvement parameters and thus whether the influence of the suggested or intended improvement will actually have a positive technical effect on the very application and system, which should be improved, taking into account the respective runtime environment of the application and/or device condition on which the application is executed (in the example above: processing and runtime will be measured and compared to current processing time and/or with other improvement requirements).

The method of at least one embodiment is computer implemented. The computer implemented method may be stored on a computer readable medium or memory. All steps are executed on a computing device or a network thereof. Thus, the method is executed by employing at least one processing entity configured to execute computer-executable instructions stored in a memory to perform the steps, mentioned above.

Another embodiment of the invention therefore also refers to a computer program with program code for executing an embodiment of the method mentioned above, upon the computer program being executed on an electronic device. The computer program may be provided via download from a server. Further, the computer program may be executed on a sever for a client by assessing a link or a http interface on a web-browser on the client.

The computer program may be processed in a distributed manner, such as that certain steps are performed on a first computing entity (e.g. at the device) and that other steps are performed on a second computing entity (e.g. on a central server).

The computer program may be offered, placed on market, used, imported and/or stored as (and thus may be part of) a computer program product. Thus, the computer program may be provided on a non-transitory storage medium (computer readable medium, like a computer disc or a memory stick etc.). Alternatively, the computer program may be provided via download via a respective network connection to a server, which stores the computer program by providing a link to the server with the computer program stored thereon. A "computer-readable medium" or "storage medium" can be any device that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium can include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CDROM).

The term "computer" refers to any electronic device comprising a processor, such as a general-purpose central processing unit (CPU), a specific purpose processor or a microcontroller. The processor is adapted to execute a special computing task, namely for providing the load skewness result. A computer is capable of receiving data (an input), of performing a sequence of predetermined operations thereupon, and of producing thereby a result in the form of information or signals (an output). Depending on context, the term "computer" will mean either a processor in particular or can refer more generally to a processor in association with an assemblage of interrelated elements contained within a single case or housing.

The systems and methods described herein may be embodied by a computer program or a plurality of computer programs, which may exist in a variety of forms both active and inactive in a single computer system or across multiple computer systems. For example, they may exist as software program(s) comprised of program instructions in source code, object code, executable code or other formats for performing some of the steps. Any of the above may be embodied on a computer readable medium, which include storage devices and signals, in compressed or uncompressed form.

According to a preferred embodiment, the improvement result is used to automatically generate a set of computer instructions to be executed in the runtime environment. The so generated computer instructions for implementing the improvement result may optionally and in a preferred embodiment only be executed in reply to a confirmation signal, issued by the device and/or by a central improvement node, acting as administration node. The confirmation signal serves to indicate that the computed improvement result should be put into practice and implemented and be thus executed on the device.

According to another preferred embodiment, the detected state is used to determine at least one target object (which may be provided as digital target object entity), which comprises at least one pre-calculated improvement target for the device with respect to the detected state. The target object may be provided as prioritized queue, representing a list of prioritized improvement targets.

In an embodiment, the method may comprise to detect requirements which need to be met by the improvement candidates. Requirements may be predefined or may be configured in a configuration phase each time (in particular for each improvement) anew. The candidate improvement results are tested with respect whether or not they comply with the detected requirements. As an advantage only relevant candidates are presented as improvement result. Thus, the method provides a selection of improvement results, which are requirement conform.

According to another preferred embodiment, the steps of test-wise execution, measuring and adding are executed iteratively for each candidate of the retrieved candidate improvement result to provide the improvement result. This has the advantage that the improvement result may comprise a set of dedicated candidates, each matching the specific requirements and that also more than one candidate may be suggested as improvement result.

According to another preferred embodiment, all added candidates of the improvement result are prioritized according to their measured improvement parameters to generate a prioritized improvement result. This helps to improve quality of the computed improvement result.

According to another preferred embodiment, the improvement result comprises a new-install instruction to newly install an application on the device, a configuration instruction to apply a new configuration of an installed application, a replacement instruction for replacing an installed application with a replacement application, an add-instruction for provisioning of additional data sources with its interfaces and/or new functions to be activated in an installed application. As an advantage, the improvement result may be very comprehensive, including and wide-ranging by comprising a plurality of different types of improvement measures and actions.

According to another preferred embodiment, the improvement parameters are measured dynamically on real life data of the device and thus in the context of the medical imaging device. This feature improves quality as improvements are based on real life data.

According to another preferred embodiment, the status comprises to automatically detect or identify parameters, indicating: installed applications, a number of logged-on users, used formats, access rights, roles, user context data, physical and logical parameters of the device, comprising scanner parameters, like dose used for computer tomographic imaging devices, protocol usage, image quality and others. The parameters to be considered for the status are preferably pre-configured and may be dynamically amended according to user's preferences.

According to another preferred embodiment, the improvement result is used to provide an installation package, dedicatedly designed to be installed on the respective device with its runtime environment. This has the advantage that the improvement result may be put into practice and may be implemented on the device easily (one click improvement).

According to another preferred embodiment, the improvement result is stored in a database so that it is accessible and useable as reference improvement result for other devices for retrieving the candidate improvement result. This provides the option that improvements on comparable devices and runtime environments that have been evaluated as appropriate and in conformance with technical requirements may also be used for other devices, too (benchmarking improvement).

According to another preferred embodiment, the step of retrieving the at least one corresponding candidate improvement result is done by executing a correlation algorithm for finding correlations of usage patterns on other devices, other runtime environments and/or other user contexts. The correlation algorithm may be based on a similarity concept and/or on a recommendation concept. The correlation algorithm matches devices and applications residing on the devices or matches devices and accessed data (studies, cases) or matches devices and user profiles and workplaces or matches operational details on the device (e.g., scan protocols used, body regions scanned, number of re-scans, acquired image types (CT, PET/CT, MR, MR/PET), usage of image rendering and manipulation tools (e.g., MIP, MPR, 2D, 3D, 4D), diagnostic details from the clinical reports like lesions or cancer or fractions etc.) against application capabilities and functionalities. The correlation algorithm may also use a set of the above single match steps to characterize a device and an application and match such sets against each other to, for example, calculate the correlation between devices, devices and applications, or between applications. The correlation calculation preferably uses algorithms for detecting similarity of the respective objects (mentioned above by way of example).

Another embodiment of the application is directed to a cloud-based improvement node for computing an improvement result for a runtime environment of at least one application, on a device in a medical context, comprising:
    a state interface which is adapted to detect a state of the runtime environment on the device;
    a database interface to a database in which a correlation is stored between states, improvement targets and corresponding candidate improvement result, so that the database may be accessed with the detected state in order to retrieve at least one corresponding candidate improvement result;
    a test infrastructure which is provided for each of the different devices dedicatedly by representing the detected state of the runtime environment of the device and which is used for test-wise execution of the retrieved candidate improvement result;
    a measurement unit which is adapted to measure improvement parameters during the test-wise execution on the test infrastructure; and
    an output interface which is adapted for providing the improvement result, wherein the improvement result comprises those candidate improvement results for which the measured improvement parameters meet predefined requirements.

Another embodiment of the application is directed to a system for computing an improvement result for a device within a network of devices to be used in a medical context, the system comprising: an improvement node according to an embodiment of the application;
    a plurality of devices, each having its runtime environment for execution of a plurality of applications; and a database.

A result, in at least one embodiment, is an electronic object which serves as final result of the computation and may comprise an indication together with computer executable instructions for the runtime environment. The indication may be provided in textual form. The computer instructions are directly executable on the target device. The improvement may relate to installation of a new application, to a replacement of an application with another application, a replacement or addition of a function and addition of new data sources with respective interfaces etc. An indication may be provided in addition as e.g. a screenshot, representing the reasons for improvement and thus shows the user why the improvement was initiated.

For example, for dose management at a device for a scan workplace, the device doesn't have any application for dose management installed. The user is provided with an improvement result that e.g. shows in a screenshot that dose outliers have been detected in the scan data that come from this device. Dose outliers require corrective actions by the user, and the improvement allows the user to install a new application that calculates and shows dose outliers. Another such improvement result can be to suggest an improved application, which calculates and shows new scan protocols, used on other devices, where the scans have not shown outliers, and where the protocols also work for the current scan device type of this user, because the scan conditions are similar (manufacturer and device type, body region, etc.). Thus, preferably context conditions are considered for computation of the candidate improvement result and the final improvement result.

The candidate improvement result serves as preliminary result of the computations and thus is a preliminary suggestion for an improvement result, which first needs to be tested whether it results in a real improvement for the target system in the respective runtime environment by measuring the improvement parameters during execution in the test infrastructure.

The test-infrastructure is generated such that the candidate improvement result (e.g. an app) may be executed as a hidden service on the target device or system. The test infrastructure may be deployed on a server (cloud-based) or even on the target device itself.

The target device is the device on which the application runs which is to be improved and/or on which the runtime environment to be improved is provided. The target device may be a system with hardware and/or software modules.

The state of a runtime environment refers to all aspects and parameters of the runtime environment, comprising state values that are accessible during program execution, but also active entities that can be interacted with during program execution like disk drives and touchpads or keyboards. For example, environment variables are features of many operating systems, and are part of the runtime environment; a running program can access them via the runtime system. Likewise, hardware devices such as a DVD drive are active entities that a program can interact with via a runtime system. The state also comprises parameters, indicating which applications (apps) are installed, which settings and configurations do apps have, which role of the user; device context, which data are accessible, what improvement areas exist, e.g. Dose/Usage/Protocols/Images, indications what medical device type e.g. CT/MRT/Ultrasound/Reading, what types of medical data is accessible e.g. DICOM/HL7/study data and what organs, what non-medical data is accessible e.g. scanner usage data/patient change times, what is the organizational structure e.g. institutions/departments, both for user and devices, what is the technical structure e.g. receivers/services types/license types/data repositories, what medical data sources are connected e.g. PACS, what devices are used by users e.g. desktop/mobile.

The improvement parameters may be pre-configurable and are depending on the functionality of the system to be improved. If the device or system to be improved is e.g. a CT scanner, a set of parameters may for example comprise dose regimes, dose exposures for the patient, quality of acquired images, examination times, etc.

The improvement target (in short also: target) is more complex than the improvement parameters and usually comprise a set of technical improvement parameters referring to the device, to its hardware and/or software, in particular being an imaging device. A target may also relate to the software applications, implemented on the device. A target may comprise additional interfaces, access to other protocols, application updates or new software versions, etc. The target is stored in an improvement target object, which is a data structure, representing associated respective actions or measures. The improvement targets are determined by accessing a database with stored relations between an application, its detected state and pre-configured improvement targets.

A target object, is a data structure for storing and transmitting at least one improvement target. The target object thus indicates an improvement potential in general. The improvement target may be pre-calculated for each application in its detected state.

Preferably, each of the applications is pre-processed in that an application object is generated for the application which might comprise a meta data file. The meta data file comprises a target object, which indicates an improvement potential. The improvement potential may refer to different improvement targets.

The invention will now be described in the context of several embodiments. A first embodiment is represented in FIG. 1.

A central improvement node 10 serves to provide the improvement functionality and respective applications. The improvement refers to at least one device D, which comprises a computing entity and is adapted to be executed in a medical context. Usually several such devices D1, D2, D3, . . . Dn are associated over a network NW to the improvement node 10. The device D may comprise or be an imaging entity, like e.g. a CT or MRT scanner or a post processing entity. The devices D comprise a runtime environment RTE in which at least one application A is executed. As shown in FIG. 1 on the right side, typically several applications A may be run in such a runtime environment RTE. Further, more than one runtime environment RTE may be provided on one single device D.

The improvement node 10 comprises different interfaces for message transfer and communication with external devices and entities. In particular, it comprises a state interface 11 which is adapted to detect a state st of the runtime environment RTE on the device D. A database interface dbi is further provided to a database DB in which a correlation is stored between states st, improvement targets t and corresponding candidate improvement results c, so that the database DB may be accessed with the detected state st in order to retrieve at least one corresponding candidate improvement result c.

The improvement node 10 comprises requirement interface 18 which is adapted to receive requirements req. The received requirements req are needed on the improvement node 10 for computation of the improvement result r. The requirements req may be defined on the device D or on another node (for example an administration node, not shown in FIG. 1). The two alternatives for providing the requirements req are depicted in FIG. 1 with dotted lines. The requirements req may also be extracted from a storage or a database DB.

For processing the result r, the improvement node 10 comprises a test infrastructure 14, which is provided for each of the different devices D dedicatedly by representing the detected state st of the runtime environment RTE of the device D and which is used for test-wise execution of the retrieved candidate improvement result c. In this respect it should be noticed that the test infrastructure 14 may for example include hardware and software. The special test infrastructures 14D1, 14D2, . . . 14Dn should represent that the particular detected state st of the runtime environment RTE on the device D is provided and therefore multiple such test infrastructures 14 are represented. A measurement unit 15 is adapted to measure improvement parameters par during the test-wise execution on the test infrastructure 14. Preferably, it is configurable which types of improvement parameters par are to be measured, like e.g. runtime, storage resources, number of interfaces etc. In a first embodiment, shown in FIG. 1, each test infrastructure 14 is associated with a measurement unit 15. In a second embodiment, only one measurement unit 15 is provided for all test runtime environments 14, which thus serves all different test executions.

Finally, an output interface 17 is adapted for providing the improvement result r or a prioritized improvement result pr. The improvement result r comprises those candidate improvement results c for which the measured improvement parameters par meet the (predefined) requirements req. The improvement result r is transmitted to the respective client device D via result interface 17 for local execution and/or implementation.

The improvement node 10 may comprise a processing unit 13 for computational processing and execution of algorithms. The processing unit 13 may comprise the plurality of test infrastructures 14 for the respective runtime environments RTE to be improved of the device D and may further comprise the measurement unit 15. The processing unit 13 may optionally comprise a trigger unit 12, which is adapted to activating the improvement and corresponding message exchange and data transfer. In particular, it may be configured that the improvement method may be initiated on the side of the improvement node 10 and thus centrally (e.g. via a central administrative instruction) or may be initiated by the device D itself according to pre-configurable trigger parameters, e.g. if the performance is evaluated to be under a pre-defined lower limit or if storage capacity is no longer sufficient.

Figure 2:
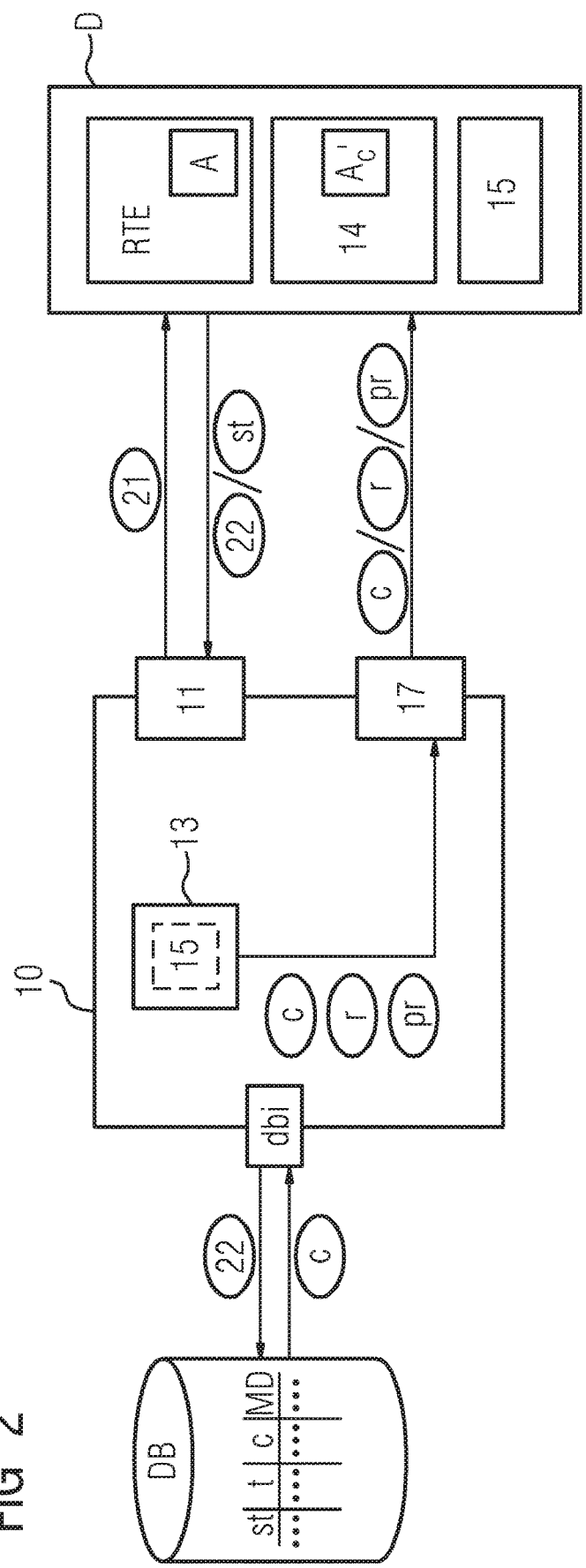
FIG. 2 is another example of an implementation of the improvement node in a network.

FIG. 2 shows another embodiment in which the test infrastructure 14 for test wise execution of the candidate result and the measurement unit 15 are both provided locally on the respective device D. The server or improvement node 10 only comprises the processing unit 13 for which is responsible for receiving the candidate improvement results c from the dataset retrieval with status data st. The candidate improvement result c is then executed as a hidden service on the local device D. "Hidden" in this respect means that the user will not be aware of execution of the application in a candidate improved version $A'_C$, for testing purposes. The execution of the candidate version $A'_C$ is executed in an especially provided test infrastructure 14. During test wise execution, the improvement performance parameters par are measured by way of the measurement unit 15, which in this example is also provided on the local device's site D. However, in another embodiment, the measurement unit 15 may be provided as a service on the server node 10. In FIG. 2 this should be depicted with the dotted lines of block 15 on server 10. The result of the test wise execution and the measured improvement parameters par may be aggregated in a test message 22 which will be transferred back to the central server 10 for further processing. In particular, the received test messages 22 which are evaluated to be conform with the requirements req may be prioritized for generating the final result to be provided to the device D. The database DB may be of several types. If it is provided as relational database, associations between, status st, improvement target t, candidate improvement result c and/or metadata MD may be referenced and retrievable.

Figure 3:
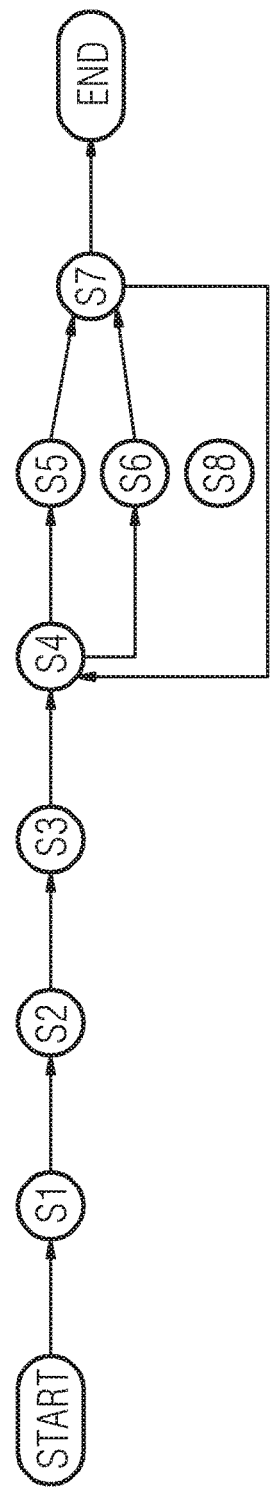
FIG. 3 is a flow chart of an improvement method according to a preferred embodiment of the invention.

FIG. 3 represents a flow diagram for a flow of method steps. After start of the improvement method, the state st of the runtime environment RTE is detected in step S1.

Step 2 is optional. In step S2 the improvement target may be calculated or may be detected and retrieved from a special data structure, namely the target object TO, in which improvement targets TO for the applications and its runtime environments RTE are already specified. In this case, the database DB might be assessed in step D3 directly with the improvement target t.

In step S3 the database DB is assessed with the detected state st for retrieving a list of candidate improvement results c in step S4. In step S5 each of the candidate improvement results c is executed in a test infrastructure 14 and improvement parameters par are measured in step S6. Typically steps S5 and S6 are executed in parallel. The measured improvement parameters par are evaluated whether or not they comply with the requirements req. In case the requirements are met, the respective candidate is added to the final improvement result in step S7. Typically, the steps S5, S6 and S7 are executed iteratively, which is depicted in FIG. 3 with reference numeral S8. After this the method may end or may be reiterated.

Figure 4:
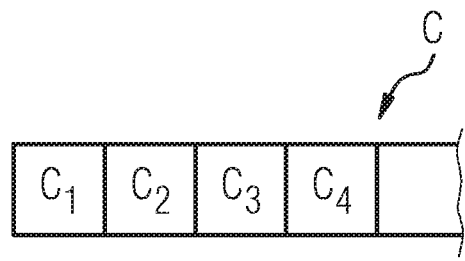
FIG. 4 shows a schematic representation of a candidate improvement result.

FIG. 4 shows a schematic representation of a candidate improvement result c with its elements or candidates $c_1, c_2, c_3, \ldots$.

Figure 5:
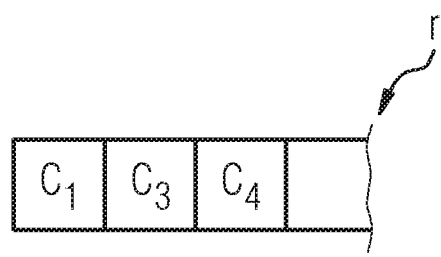
FIG. 5 shows a schematic representation of an improvement result.

FIG. 5 shows a schematic representation of a (final) improvement result r. As can be seen in the example, $c_2$ has been evaluated during measuring and later assessment with respect to the fulfillment of the requirements req, that it should not be comprised in the result dataset r.

Figure 6:
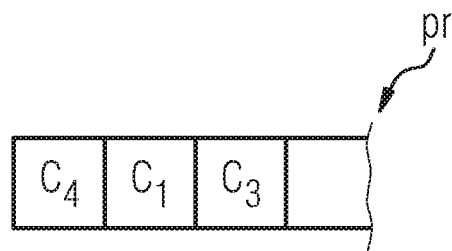
FIG. 6 shows a schematic representation of a prioritized improvement result and FIG. 7 shows an example data structure for a target object.

FIG. 6 shows a schematic representation of a prioritized improvement result pr. Here, it can be seen, that the improvement result r, shown in FIG. 5, was re-ordered and re-structed, so that the fourth candidate c4 now should be executed as first measure on the device D, because it was judged to have the maximal technical influence according to the measured improvement parameters par on the runtime environment RTE of the device D.

Figure 7:
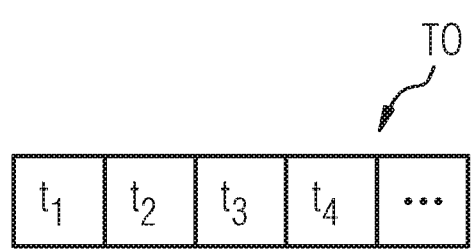

FIG. 7 shows a schematic representation of a target object TO with its various elements $t_1, t_2, t_n \ldots$.

In contrast to prior art system, the trigger for action for improvement is dynamic in the proposed solution. The trigger is multi-fold, e.g. a user starts working on a case for diagnosis or prepares a scheduled procedure at the acquisition workplace, while medical data from the last hour show dedicated outliers or show best-of-breed usage times, or usage patterns from equivalent users have been detected dynamically and shall be used as de-facto standard in the hospital, or nation-wide medical standardization needs to be followed-up in the clinical routine work. These exemplary scenarios indicate that it is far to complex for a pre-planning approach, meaning also too much complexity for the human mind. This requires an automated technical solution.

In general, the proposed improvement solution, as its first characteristics, calculates and re-calculates such internal and external data related triggers e.g. from the above sources, and, as its second characteristics, can inject a number of TargetOptionVortex (TOV). A TOV is a meta product which serves as candidate improvement result for giving priority to only a selection of improvements. And, as its third characteristics, the proposed solution (with the method claimed) matches the first two to the application landscape and usage patterns, which can be measured and retrieved for each user, to provide the users (and/or their administrators) with guidance for multi-dimensional improvements. Such multi-dimensional improvements can e.g.—and as already mentioned above—embody the installation of new apps, using already installed apps, using dedicated apps with a configuration that exactly matches the user's working context, and others, providing both the reason why such improvement is realistic and how to at-once realize this improvement (e.g. with one click on a dynamically auto-calculated setup for this user). Now, the user can select a personalized working setup and environment, and is still governed by the hospital IT-administrational requirements and regulations, and the legal background of medical devices is taken into account.

Core part of the concept is to create an automated, bi-directional guidance to the users of medical and/or non-medical devices D, for e.g. improvements, with Apps-as-a-Service as paradigm (with apps that are used or unused) and the TOV approach. The TOV act as artificial meta-products in an application store and thereby become first class citizens in the approach. Thus according to the improvement method, only relevant improvements are suggested, which are in fact perceivable by the user and thus have a technical impact on the respective device D, which may be measured (performance time etc.) Further, there are automatic correlations with real medical data from the real user (personal) context. The improvement is measured automatically in the real user data context, and the result is presented at the user's workplace. One important feature of the technical solution is to automatically and dynamically detect the e.g. missing application in the user's work context with 'App-as-a-Service' paradigm. So, the 'missing' and new app is used as a hidden service to prove the usefulness of the novel app for the user context, and then suggest this app for immediate usage to the user as improvement result r or part thereof. Another important feature is the TOV and related TOV-algorithms to extract new contents from existing data sources, the TOVs (contain reason for improvements) that provide the guidance focus for one automated improvement procedure, and the algorithms and services that can calculate and predict improvements, which then result in changes to the user's work setups and working model.

In a preferred embodiment a Real-Time Med Guide Mediation is provided with its sub-components and which functions as the core computational part that connects the TOV-input with a Med Guide Data Lake and the user sessions, and the users, all based on new purpose driven med guide algorithms. The Apps are executed with the App-as-a-Service paradigm, based on the TOV-defined input data, and the benefit/improvement etc. is calculated with automated algorithms, and if the TOV-based benefit-statement is met, the e.g. screenshot from the respective App is ready and can be sent to the user's workplace D. The Med Guide Data Lake is a dedicated mixture of medical, non-medical and user centric, hospital devices D, which is required to run the novel med guide algorithms.

The Med Guide Vendor Data repository is an open space, e.g. as input channel, and in fact an extension to the app store that contains apps of vendors. It contains e.g. TOV data, both finished (reusable) TOV and meta data in app store quality that is used to build TOV entities. Finished TOV can be activated in the Med Guide Data Lake for processing. Here, new and updated Apps and TOV-sets can be submitted altogether, and the Apps then are executed with the App-as-a-Service paradigm. The user gets e.g. a Link to install the App at his/her workplace, to realize measured benefits/improvements in his/her work context.

The Med Guide Dashboard repository is the output channel to hold and store results from the med guide algorithms and from TOV-driven actions (e.g. improvement 'campaigns') in the user space. The Audience Estimator mainly is the primary med guide algorithm to help the Real-Time Med Guide Mediation to transform a TOV into the hospital and user space and thereby calculate a potential hit rate for output, e.g. the number of users that can use the improvements and the probability (e.g. from previous sessions) that the improvements are accepted by users. The new real-time med guide algorithms are executed by the above components to perform the following tasks continuously 1. Explore and prepare med data lake continuously.
   a. Prepare raw data lake, e.g. non-medical KPIs from PACS (like teamplay today, and with more abstractions)
   b. Prepare a med data lake, that is suitable for TOV-based targeting (e.g. find correlations between users and devices/workplaces, users and used-apps, users and studies/cases)
2. Collect and calculate vendor related and technical data continuously
   a. Apps, usage formats and data, user/role targeting, improvement potential, e.g. calculate trend data for TO that can be used for successful TOV
3. Match in real-time
   a. Apps-as-a-Service as technical paradigm, usage formats, user/role targeting, improvement potential, with available data in med data lake
   b. Improvement-based queue for each targeting option
   c. Currently logged-on users are the focus for near-real-time improvement outputs with data that is relevant to them.

The following detailed list depicts the known examples of Targeting Options (TOs) that trigger the algorithms in the infrastructure and the valid TOs are pre-selected by external or internal sources (IT admin, also made available by medical device vendors, medical app vendors, etc.). Thereby, the user's activity and work context can be pre-analyzed and then addressed for auto-calculated improvements, by different parameters:

By medical keywords (in DICOM Header)
By medical KPIs: Dose, Usage (see more on subsequent slides)
By medical equipment
By patient diseases (SNOMED/ICD), also by population (pop. health)
By medical institution
By medical apps installed
By medical apps used (e.g. at least once a month for at least 1 min)
By benchmarking (e.g. top 10% in Dose Exposure in its region . . . )
By number of Receivers installed/not yet installed
By privacy level set:
By amount of studies by modality uploaded since date X with privacy level
By number of/availability of users affiliated with an institution/not yet affiliated with an institution
By language setting
By number of locations
By licenses available (free licenses, premium licenses)
By number of study shares in Images (received, shared)
By number of active users in Institution
By number of pageviews per month in Institution (also, in Dose App, in X App . . . )
Dose related parameters:
  By Dose Targets set (internal, national)
  By number of Dose Events above internal reference in a time period
  By number of Dose Events above national reference in a time period
  By number of exams by DLP (mGy cm) in a time period
  By number of exams (on a device type) by modality in a time period
  By number of exams (on a device type) by modality in a time period
  By body regions (on a device type) by modality in a time period
  By (number of) operators (on a device type) by modality in a time period
  By internal/national reference level→modality→body region→phantom size (e.g. Adult16)→CTDIvol-max (mGy)
By Usage related parameters:
  By number of patients by modality by body region in a time period
  By number of exams by modality by body region in a time period
  By average exam duration by modality by body region in a time period
  By average patient change time by modality by body region in a time period
  By number of exams per patient by modality by body region in a time period By number of exams per hour (in all hours, in working hours) by modality by body region in a time period By table occupancy by modality in a time period By body regions by exam count (chest, neck, head) in a time period By procedure types by exam count (CT chest, CT head) in a time period By number of protocols by exam count (P1 used in 300 exams) in a time period By (number of) operators by exam count (O1 did 2333 exams) in a time period By Protocol related parameters By activity history of protocols by scanner (e.g. #changes in a time period)

The above list is publicly available and can be re-used in all TargetOptionVortex (TOV) creations, and the list is extended by internal and external sources.

In the following an example for a TargetOptionVortex (TOV) as meta-product, with an open structural definition, is provided. For example:

New App name (see e.g. the 'advanced app')

app-input live data, and app default exposure (for applying the App-as-a-Service paradigm)

user-matching data: group, role, apps and functions hospital/institution/department-matching data related apps/base apps/previous apps and functions visibility pattern ('at login') and/or improvement quantification: type, value, unit etc.

For example, the IT-Admin creates the exposure plan per TargetOptionVortex (TOV), to make it visible to the users of the devices D.

The improvement result r, in general, is a user specific install or update package, exactly designed for his work environment and the current device D.

The platform in the background can be triggered to re-use TargetOptionVortex elements (TOV) at any time, also based on a plan from the IT-Admin, e.g. as a housekeeping device for the hospital's app landscape.

In a preferred embodiment, it is sufficient to send a screenshot to the user workplace, because the screenshot already shows real e.g. improvements, and no additional installation is required at the same time (and therefor doesn't break e.g. the status of a medical device D of the user's workplace).

An active and automated feedback channel shows the acceptance level of the TOV based improvements, and the relevance of existing guidance and improvements can be re-assessed in future, because the activated TOVs and their results form a technical history record of the work place evolution. With other words, the term 'bidirectional' refers to the communication between the improvement node 10 and the device D. Not only the improvement result r is sent in a first direction from the node 10 to the device D but also a confirmation signal is sent back from the device D to the improvement node 10, indicating whether or not and to what extent the suggested improvement result r was accepted by the user of the device D. The confirmation signal serves as a kind of feedback signal, which could be used for training the improvement method on the node 10.

In the following, an example of a TO and TOV objects are given with respect to improvement relating to a dose of e.g. a medical device D.

A Targeting Option TO may e.g. be "Dose Exposed is higher than National Threshold in >20% of the cases over the last 3 months".

The following Targeting Details may be provided.

a. [Data] Only consider scanners that produce RDSR data because this data is reliable b. [Data] Do not consider Black Image data because that data is not very reliable as OCR is employed to pull the Dose Data from the DICOM Image c. [Apps] Only consider Institutions that use the Basic Dose App on a regular basis A TargetOptionVortex TOV may e.g. comprise the following details:

a. Promoted: Advanced Dose Guide with Specialized Dose Data Evaluation Capabilities b. TOV format: image, 6 sizes c. TOV to be shown on devices: all d. TOV to be shown in browsers: all The application preferably comprises a front end with a user interface, which may be provided as graphical user interface.

For example, a Dose Control Application may be provided in at least two different versions. In a first version examinations cross devices D are counted, and all outliers are shown and depicted, e.g. outliers with high Dose at the right. In a second version, the application is device specific and can show the range of applied Dose per scanner model, and for each protocol on that scanner, which is an improvement, because too much dose (the outliers) can be found on each scanner separately and for each protocol separately, and this isn't possible in the first version, explained above. The respective results r may be provided as screenshots to the interested recipients, like the devices D and the improvement node 10 for central storage and processing.

The scope of protection of the present invention is specified by the appended claims and is not restricted by the features explained in the description or shown in the drawing.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for computing an improvement result for a runtime environment of at least one application, the at least one application being installed on a medical device, and the method comprising:
   detecting a first state of the runtime environment on the medical device;
   accessing a first database to retrieve at least one candidate improvement result, the at least one candidate improvement result corresponding to the first state;
   performing test-wise execution on a test infrastructure based on the at least one candidate improvement result, the test infrastructure having the first state;
   measuring improvement parameters of the test-wise execution; and
   obtaining the improvement result by adding a set of candidate improvement results among the at least one candidate improvement result to the improvement result, the set of candidate improvement results including one or more among the at least one candidate improvement results for which the improvement parameters meet a criterion.

2. The method of claim 1, further comprising:
   generating a set of computer instructions to be executed in the runtime environment based on the improvement result.

3. The method of claim 2, wherein generating a set of computer instructions generates the set of computer instructions in response to a confirmation signal issued by at least one of the medical device or a central improvement node.

4. The method of claim 2, wherein
   the at least one candidate improvement result includes a plurality of candidates improvement results;
   the performing performs the test-wise execution on a respective candidate improvement result among the plurality of candidate improvement results;
   the measuring measures corresponding improvement parameters of the test-wise execution on the respective candidate improvement result;
   the obtaining includes adding the respective candidate improvement result to the improvement result in response to determining the corresponding improvement parameters meet the criterion; and
   the method further comprises iteratively executing the performing, the measuring and the obtaining for each of the plurality of candidate improvement results to obtain the improvement result.

5. The method of claim 2, wherein
   the at least one candidate improvement result includes a plurality of candidates improvement results;
   the set of candidate improvement results includes two or more candidate improvement results among the plurality of candidate improvement results; and
   the method further comprises prioritizing the two or more candidate improvement results based on the improvement parameters to obtain a prioritized improvement result.

6. The method of claim 2, wherein the accessing a first database comprises executing a correlation algorithm for calculating correlations of usage patterns on at least one of other devices, other runtime environments or other user contexts.

7. The method of claim 6, wherein the correlation algorithm is based on at least one of a similarity concept or a recommendation concept.

8. The method of claim 1, further comprising:
   determining at least one target object based on the first state, the at least one target object including at least one improvement target for the medical device, and the at least one improvement target corresponding to the first state,
   wherein the at least one candidate improvement result retrieved from the first database corresponds to the at least one improvement target.

9. The method of claim 8, wherein
   the at least one candidate improvement result includes a plurality of candidates improvement results;
   the performing performs the test-wise execution on a respective candidate improvement result among the plurality of candidate improvement results;
   the measuring measures corresponding improvement parameters of the test-wise execution on the respective candidate improvement result;
   the obtaining includes adding the respective candidate improvement result to the improvement result in response to determining the corresponding improvement parameters meet the criterion; and
   the method further comprises iteratively executing the performing, the measuring and the obtaining for each of the plurality of candidates improvement results to obtain the improvement result.

10. The method of claim 8, wherein
    the at least one candidate improvement result includes a plurality of candidates improvement results;
    the set of candidate improvement results includes two or more candidate improvement results among the plurality of candidate improvement results; and
    the method further comprises prioritizing the two or more candidate improvement results based on the improvement parameters to obtain a prioritized improvement result.

11. The method of claim 8, wherein the accessing a first database comprises executing a correlation algorithm for calculating correlations of usage patterns on at least one of other devices, other runtime environments or other user contexts.

12. The method of claim 11, wherein the correlation algorithm is based on at least one of a similarity concept or a recommendation concept.

13. The method of claim 1, wherein
    the at least one candidate improvement result includes a plurality of candidates improvement results;
    the performing performs the test-wise execution on a respective candidate improvement result among the plurality of candidate improvement results;
    the measuring measures corresponding improvement parameters of the test-wise execution on the respective candidate improvement result;
    the obtaining includes adding the respective candidate improvement result to the improvement result in response to determining the corresponding improvement parameters meet the criterion; and
    the method further comprises iteratively executing the performing, the measuring and the obtaining for each of the plurality of candidate improvement results to obtain the improvement result.

14. The method of claim 1, wherein
the at least one candidate improvement result includes a plurality of candidates improvement results;
the set of candidate improvement results includes two or more candidate improvement results among the plurality of candidate improvement results; and
the method further comprises prioritizing the two or more candidate improvement results based on the improvement parameters to obtain a prioritized improvement result.

15. The method of claim 1, wherein the improvement result comprises at least one of:
a new-install instruction to newly install new application on the medical device,
a configuration instruction to apply a new configuration of a first installed application,
a replacement instruction for replacing a second installed application with a replacement application, or
an add-instruction for provisioning of additional data sources, the provisioning of the additional data sources including activation of corresponding interfaces and new functions in a third installed application.

16. The method of claim 1, wherein the measuring dynamically measures the improvement parameters based on data of the medical device.

17. The method of claim 1, wherein the first state includes parameters indicating: installed applications, a number of logged-on users, used formats, access rights, roles, user context data, physical parameters of the medical device and logical parameters of the medical device.

18. The method of claim 1, further comprising:
providing an installation package based on the improvement result, the installation package being configured to be installed on the medical device with the runtime environment.

19. The method of claim 1, further comprising:
storing the improvement result a second database.

20. The method of claim 1, wherein the accessing a first database comprises executing a correlation algorithm for calculating correlations of usage patterns on at least one of other devices, other runtime environments or other user contexts.

21. The method of claim 20, wherein the correlation algorithm is based on at least one of a similarity concept or a recommendation concept.

22. An improvement node for computing an improvement result for a runtime environment of at least one application, the at least one application being installed on a medical device, and the improvement node comprising:
a state interface configured to detect a first state of the runtime environment on the medical device;
a database interface configured to access at least one candidate improvement result from a database, the database storing a correlations between states, improvement targets and candidate improvement results, and the at least one candidate improvement result corresponding to the first state;
processing circuitry configured to
implement a respective test infrastructure for each of a plurality of different devices, the respective test infrastructure representing a detected state of a runtime environment of a corresponding device among the plurality of different devices, and the respective test infrastructure being configured to perform test-wise execution of the at least one candidate improvement result, and
measure improvement parameters during the test-wise execution on the respective test infrastructure to obtain an improvement result, the improvement result including one or more candidate improvement results among the at least one candidate improvement result for which the improvement parameters meet a criterion; and
an output interface configured to provide the improvement result.

23. A system for computing an improvement result for a medical device within a network of medical devices, the system comprising:
the improvement node of claim 22;
a plurality of devices, each of the plurality of devices including a respective runtime environment for execution of a plurality of applications; and
a database.

24. A non-transitory computer readable medium storing a computer program that, when executed on an electronic device, causes the electronic device to execute the method of claim 1.

25. A non-transitory computer readable medium storing a computer program that, when executed on an electronic device, causes the electronic device to execute the method of claim 2.

26. A non-transitory computer readable medium storing a computer program that, when executed on an electronic device, causes the electronic device to execute the method of claim 8.

* * * * *